(12) United States Patent
Dahlinger

(10) Patent No.: US 7,892,237 B1
(45) Date of Patent: Feb. 22, 2011

(54) SURGICAL ACCESS DEVICE AND METHOD

(76) Inventor: Eric Dahlinger, 181 Meadowlark Dr., Hawthorn Woods, IL (US) 60047

(*) Notice: Subject to any disclaimer, the term of this patent is extended or adjusted under 35 U.S.C. 154(b) by 934 days.

(21) Appl. No.: 11/076,145

(22) Filed: Mar. 9, 2005

Related U.S. Application Data

(60) Provisional application No. 60/551,424, filed on Mar. 9, 2004.

(51) Int. Cl.
*A61F 2/46* (2006.01)

(52) U.S. Cl. .................................................. 606/86 R

(58) Field of Classification Search ............. 606/86, 606/96, 104, 192, 194, 198, 90, 95, 99, 4; 604/164.1, 164.03, 174–175, 264, 908, 910, 604/912, 104, 180; 600/208
See application file for complete search history.

(56) References Cited

U.S. PATENT DOCUMENTS

| | | | | | |
|---|---|---|---|---|---|
| 3,331,371 | A | * | 7/1967 | Rocchi et al. | 604/99.04 |
| 4,464,175 | A | * | 8/1984 | Altman et al. | 604/99.01 |
| 5,030,199 | A | * | 7/1991 | Barwick et al. | 600/29 |
| 5,593,384 | A | * | 1/1997 | Halem | 604/514 |
| 5,624,395 | A | * | 4/1997 | Mikhail et al. | 604/99.04 |
| 5,658,310 | A | * | 8/1997 | Berger | 606/192 |

* cited by examiner

*Primary Examiner*—Thomas C Barrett
*Assistant Examiner*—Michael J Araj
(74) *Attorney, Agent, or Firm*—Hayes Soloway P.C.

(57) ABSTRACT

A surgical access device includes a tubular housing having two ends. Each end of the tubular housing has an opening there-through. A malleable bulbous exterior region is present along a portion of the tubular housing. The malleable bulbous exterior region is sufficiently adaptable to be compression fit within a bone tunnel. A flanged opening is provided at one of the ends of the tubular housing. A seal may be provided integral with the flanged opening.

10 Claims, 5 Drawing Sheets

SURGICAL ACCESS DEVICE AND METHOD

CROSS-REFERENCE TO RELATED APPLICATIONS

The present application is a nonprovisional U.S. patent application, which claims the benefit of U.S. provisional application Ser. No. 60/551,424, filed on Mar. 9, 2004, the teachings of which are incorporated herein by reference.

FIELD OF THE INVENTION

The present invention relates generally to a surgical device and more particularly to an access port or sleeve for passing surgical instruments into locations within the body.

BACKGROUND OF THE INVENTION

The human knee comprises an articulation of the femur, the tibia and the patella. The femur and the tibia are maintained in a condition of stable articulation by a number of ligaments of which the principal ones are the anterior and the posterior cruciate ligaments and the collateral ligaments. The rupture of the anterior cruciate ligament (ACL) is relatively commonly encountered as a result of sporting injury or the like. This rupture leads to knee instability and can be a debilitating injury. Though less common, the rupture of the posterior cruciate ligament (PCL) can be equally disabling.

When a ligament such as the ACL is damaged or torn, a replacement ligament or graft is often installed in the knee to reconstruct the natural ligament. During reconstruction of the ACL, for instance, a tunnel is typically drilled through an anterior portion of the tibia upwardly through a tibial plateau and another tunnel is drilled from the tibial tunnel into a distal end of the femur to approximate the original or natural position of the ACL. A bone-tendon-bone autograft is then harvested, often from the patellar tendon, following standard grafting procedures. A graft is then secured in the tunnels by fixation means, such as, for example, interference screws or sutures tied to screw posts. Optionally, autografts may include the hamstrings or central quadriceps tendon Once the tibial attachment site for the ACL graft is determined, a drill guide is positioned onto the bone at the requisite positioning for drilling the tibial tunnel. A tibial drill guide mechanism guides a K-wire (wire drill) from a point below the knee joint to the former ACL tibial attachment site. A cannulated drill bit is overdrilled on the K-wire forming the tibial tunnel. The drill sleeve and guide mechanism are then removed leaving the K-wire or substituted guide pin in place. If desired, a cannulated reamer is used to broach the posterior cortex.

During the course of the above procedures, surgical instruments are repeatedly inserted into and removed from the tibial tunnel. For example, a back cutting burr is passed into and out of the hole several times to create a uniform tunnel edge, a guide pin may be substituted for the K-wire, and the geometry of the drilled hole is assessed to ensure isometry with the femoral tunnel. In addition, femoral aimers, reamers, tensiometers, and the like, may also be inserted and passed into the tibial tunnel. Care must be taken, however, not to damage or enlarge the drill hole or to create additional bone fragments, particularly, at the edge of the tunnel (which has been smoothed and chamfered) to prevent abrasion and potential damage to the graft. During the entire surgical procedure, fluid is placed into the joint via a pump or gravity to maintain distension of the capsule to improve visibility. Once the tibial tunnel is created, there is a natural and undesirable tendency for fluid to drain out of the joint, through the tunnel thus reducing joint distention and/or reducing visibility through the arthroscope and access to the anatomy. If the knee is allowed to drain to the point that it is substantially without fluids, the procedure may be delayed while proper distension is again established. Less than optimal visualization may compromise the surgical results. Currently marketed devices for sealing the tibial tunnel tend to fall out of the tibial tunnel, sometimes onto the non-sterile floor. Fluid pressure in the joint, manipulation of instruments, and gravity can cause failure of existing screw in or pressure fit devices. Some existing devices are solid and will not allow instruments to pass into the joints.

Thus, a heretofore unaddressed need exists in the industry to address the aforementioned deficiencies and inadequacies.

SUMMARY OF THE INVENTION

Embodiments of the present invention provide a system and method for improving access into a joint or cavity from the outside of a bone through a tunnel formed in the bone.

Briefly described, in architecture, one embodiment of the system, among others, can be implemented as follows. A surgical access device includes a tubular housing having two ends. Each end of the tubular housing has an opening therethrough. A malleable bulbous exterior region is present along a portion of the tubular housing. An access opening is provided at one of the ends of the tubular housing.

The present invention also includes a method using a surgical access device for improving access from the outside of a bone through a tunnel formed in the bone. The method includes: at least partially drilling a hole into a bone, the drilling used to create a bone tunnel; inserting a tubular housing within the bone tunnel, wherein a malleable bulbous exterior region of the tubular housing sits pressed against an inner wall of the bone tunnel; reaching medical instruments through a seal in the tubular housing thereby engaging in other medical activities; and removing the tubular housing.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE EMBODIMENT

Figure 1:
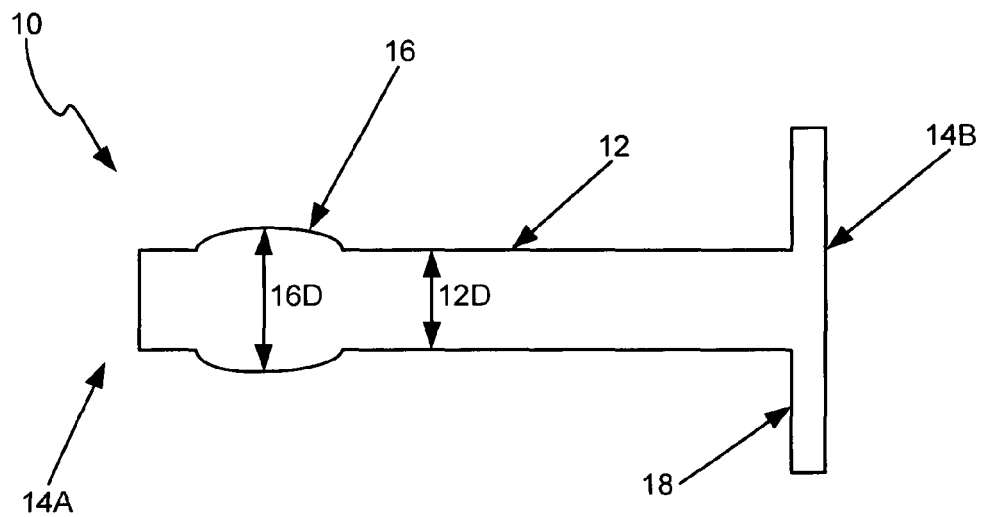
FIG. 1 is a side view of a surgical access device, in accordance with a first exemplary embodiment of the invention.
Figure 2:
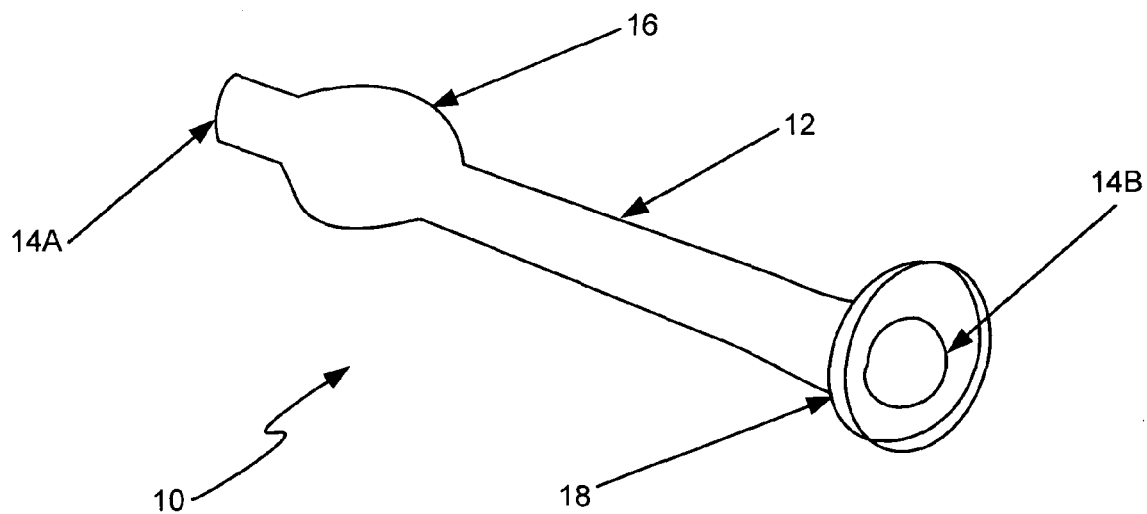
FIG. 2 is a perspective view of the surgical access device of FIG. 1, in accordance with the first exemplary embodiment of the invention.

FIG. 1 is a side view of a surgical access device 10, in accordance with a first exemplary embodiment of the invention. FIG. 2 is a perspective view of the surgical access device 10 of FIG. 1, in accordance with the first exemplary embodiment of the invention. The surgical access device 10 includes a tubular housing 12 having two ends 14A, 14B. Each end 14A, 14B of the tubular housing 12 has an opening therethrough. A malleable bulbous exterior region 16 is present along a portion of the tubular housing 12. An access opening 18 is provided at one of the ends 14A, 14B of the tubular housing 12.

As shown in the first exemplary embodiment, the tubular housing 12 may have a substantially circular cross-section, although other, varied cross-sections are contemplated by the present invention. The tubular housing 12 and the malleable bulbous exterior region 16 may, for instance, be made of a biocompatible, elastomeric material. In this embodiment, the material should be biocompatible such that the surgical access device 10 does not pose health risks when used during the procedure described herein. The material may also be flexible enough such that, the malleable bulbous exterior region 16 may be at least partially compressed when inserted, for instance, within a tibial tunnel, creating a pressure fit for the surgical access device 10 within the tibial tunnel. The malleability of the bulbous exterior region 16 may be such that the malleable bulbous exterior region 16 adapts to an inner diameter of the tibial tunnel, presses against the inner walls of the tibial tunnel while inserted, creates a substantially liquid tight seal with the tibial tunnel while inserted, and substantially regains a pre-insertion shape when removed from the tibial tunnel. The liquid tight seal limits fluid drainage from the joint through the bone tunnel at least between the inner wall of the bone tunnel and an exterior of the tubular housing 12.

As an example, the surgical access device 10 may be used to gain access to a knee, through a bone tunnel in a tibia. Bone tunnels in the tibia generally, although not exclusively, range from 8 mm to 12 mm in diameter. A surgical access device 10 designed to fit within this range of bone tunnel diameters will have a tubular housing 12 with a housing outer diameter 12D of less than 8 mm. This housing outer diameter 12D will allow the tubular housing 12 to fit within bone tunnels having the above general dimension. The surgical access device 10 designed to fit within this range of bone tunnel diameters will further have a malleable bulbous exterior region 16 with a bulbous outer diameter 16D of greater than 12 mm. The malleable bulbous exterior region 16 will be able to adapt and compress to fit within a bone tunnel of between 8 mm and 12 mm, while putting enough force on the inner wall of the bone tunnel to hold the surgical access device 10 in place and limit fluid drainage. It may further be desirable to make the bulbous outer diameter at least 13 mm, such that the malleable bulbous exterior region 16, after compression, will be able to put noticeable pressure against the inner wall of a 12 mm bone tunnel.

If multiple materials are used to make the surgical access device 10, the malleable bulbous exterior region 16 may be made from a biocompatible, elastomeric material while the tubular housing 12 is made from a different biocompatible material. The biocompatible, elastomeric material may, for instance, be a medical-grade silicone. The malleablility of the malleable bulbous exterior region 16 may be such that region is uniformly flexible. Uniform flexibility allows the malleable bulbous exterior region 16 substantially to retain its cross-sectional shape (e.g., circular) as it is forced to compress inward.

Figure 3:
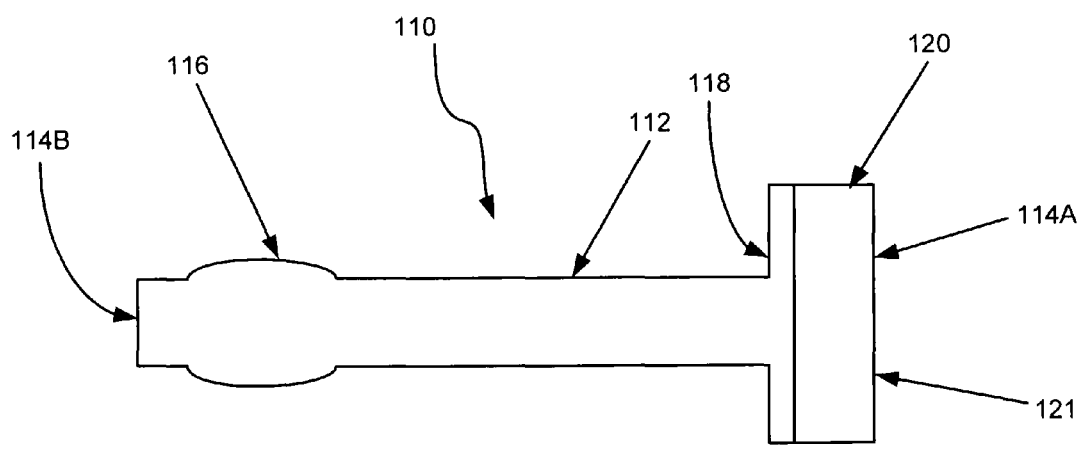
FIG. 3 is a side view of a surgical access device, in accordance with a second exemplary embodiment of the invention.
Figure 4:
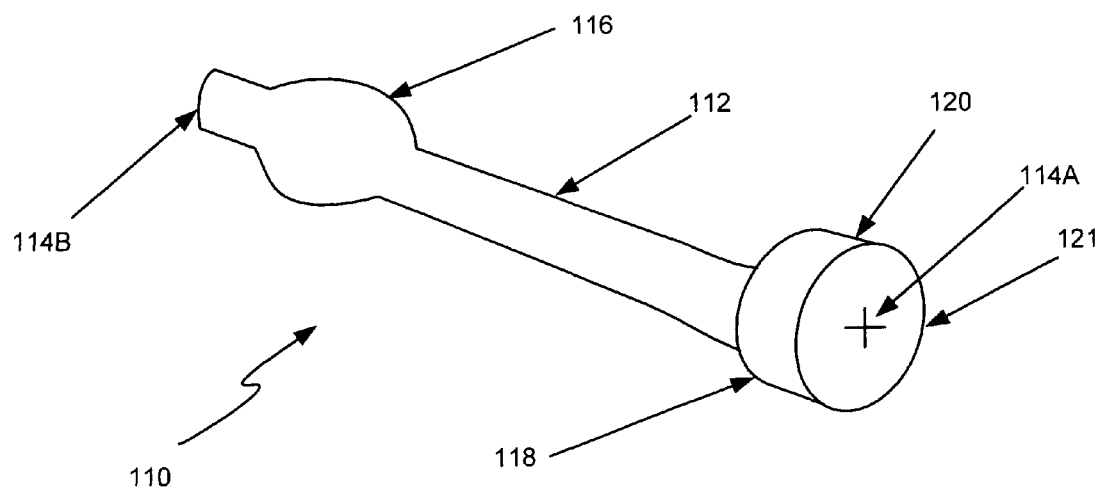
FIG. 4 is a perspective view of the surgical access device of FIG. 3, in accordance with the second exemplary embodiment of the invention.

FIG. 3 is a side view of a surgical access device 110, in accordance with a second exemplary embodiment of the invention. FIG. 4 is a perspective view of the surgical access device 110 of FIG. 3, in accordance with the second exemplary embodiment of the invention. The surgical access device 110 includes a tubular housing 112 having two ends, a proximal end 114A and a distal end 114B. Each end 114A, 114B of the tubular housing 112 has an opening therethrough. A malleable bulbous exterior region 116 is present along a portion of the tubular housing 112. An access opening 118 is provided at one of the ends 114A, 114B of the tubular housing 112.

The surgical access device 110 may be designed such that the access opening 118 and the malleable bulbous exterior region 116 are provided at disparate locations of the tubular housing 112. As shown in FIG. 3, the access opening 118 is at a proximal end 114A of the tubular housing 112 and the malleable bulbous exterior region 116 is located toward a distal end 114B of the tubular housing 112.

As shown in FIG. 3, the surgical access device 110 may include a seal 121 within the tubular housing 112. The seal 121 may be placed within a seal frame 120 extending from the access opening 118. One having ordinary skill in the art will recognize that the seal frame 120 may connect to the access opening 118, mechanically or otherwise, or it may simply be fabricated as an extension of the access opening 118. The seal 121 may be designed to close the opening through the tubular housing 112, limiting fluid drainage through the tubular housing. The seal 121 may be pliable, with a naturally closed opening there-through, whereby objects, such as medical instruments, may be pushed through the seal 121 without damage to the seal 121. Similarly, when objects are removed from the seal 121, the seal 121 may return to a naturally closed position. The seal 121 may also be made of a biocompatible, elastomeric material, such as, for instance, a biocompatible rubber. The seal 121 may be a permeable septum. The seal 121 may be attached to the seal frame 120, which may be connected to the access opening 118. Permeable septums are known to those having ordinary skill in the art and other permeable septum concepts may be incorporated without deviating from the scope of the invention.

Figure 7:
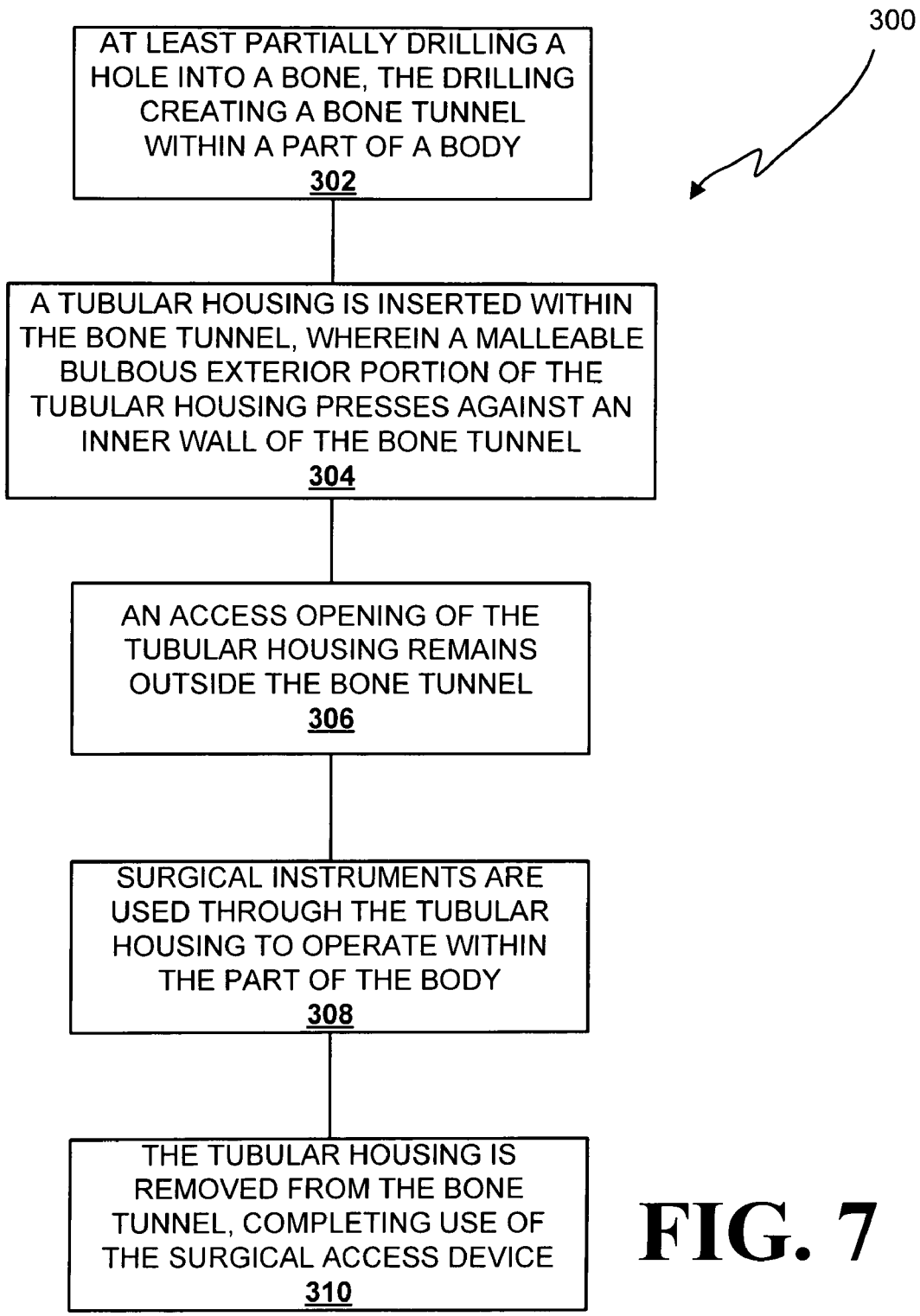
FIG. 7 is a flow chart illustrating a method of using the surgical access device of the first exemplary embodiment of the present invention.

The flow chart of FIG. 7 illustrates a method of using the surgical access device in accordance with the first exemplary embodiment of the present invention. In this regard, each block represents a module, segment, or step, which comprises one or more instructions for implementing the specified function. It should also be noted that in some alternative implementations, the functions noted in the blocks might occur out of the order noted in FIG. 7. For example, two blocks shown in succession in FIG. 7 may in fact be executed substantially concurrently or the blocks may sometimes be executed in the reverse order, depending upon the functionality involved, as will be further clarified herein.

As shown in FIG. 7, a method 300 of using a surgical access device 10 includes at least partially drilling a hole into a bone, the drilling creating a bone tunnel within a part of a body (block 302). A tubular housing 12 is inserted within the bone tunnel, wherein a malleable bulbous exterior region 16 of the tubular housing 12 sits pressed against an inner wall of the bone tunnel (block 304). An access opening 18 of the tubular housing 12 sits outside the bone tunnel (block 306). Surgical instruments may then reach through the tubular housing 12 to operate within the part of the body, engaging in medical activities (block 308). The tubular housing 12 is removed from the bone tunnel, completing use of the surgical access device 10 (block 310). The surgical access device 10 may include a seal within the tubular housing 12, integral, for instance, with the access opening 18.

Figure 5:
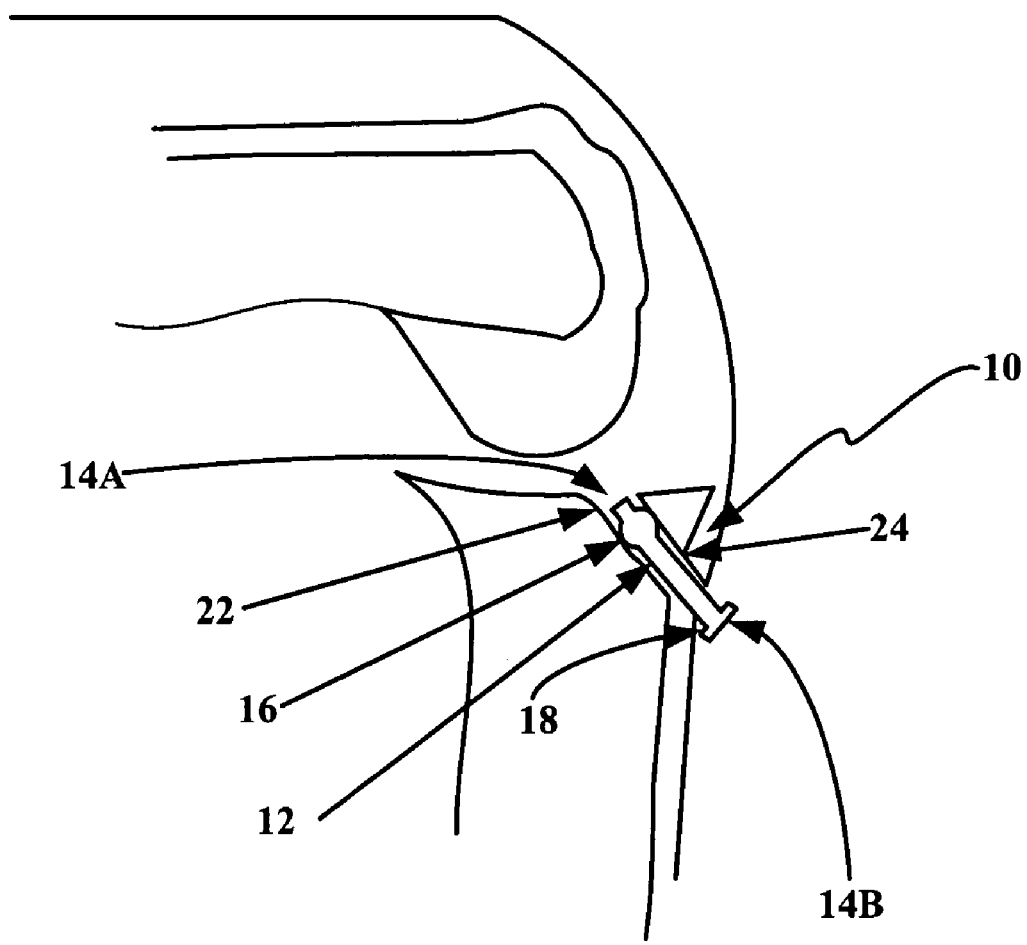
FIG. 5 is a schematic perspective view showing placement of a surgical access device in a tibial tunnel, in accordance with the first exemplary embodiment of the invention.

FIG. 5 is a schematic perspective view showing placement of the surgical access device 10 in a tibial tunnel, in accordance with the first exemplary embodiment of the invention. In use, the surgical access device 10 provides a tunnel that may be fitted within a bone tunnel, such as a tibial tunnel 22, through which to operate on the inside of a body part. The surgical access device 10 is substantially held in place within the tibial tunnel 22 by the malleable bulbous exterior region 16. The malleable bulbous exterior region 16 is sized to be compressed by the inner walls of the tibial tunnel 22 and designed to provide an elastic force outward on the inner walls of the tibial tunnel 22. This pressure fit between the malleable bulbous exterior region 16 and the inner walls of the tibial tunnel 22 holds the surgical access device 10 in place. The malleable bulbous exterior region 16 may be sufficiently flexible so as to allow it to be usable for a variety of sizes of tibial tunnels 22, which generally range from 8 mm to 12 mm in diameter. For any surgical access device 10, the tibial tunnel 22 would need to be large enough to at least accept the tubular housing 12, but narrow enough to at least partially compress the malleable bulbous exterior region 16. While compressed within the tibial tunnel 22, the malleable bulbous exterior region 16 exerts enough outward force against the inner wall of the tibial tunnel 22 to hold the access device 10 in place. The malleable bulbous exterior region 16 may also limit fluid drainage through the tibial tunnel 22. The tubular housing 12 may protect a crest 24 of the tibial tunnel 22 from the surgical instruments that are inserted into and removed from the surgical access device 10.

In the first exemplary embodiment, the access opening 18 may be placed outside of the tibial tunnel 22. The access opening 18, at a widest area, may be of greater diameter than an opening to the tibial tunnel 22.

Figure 6:
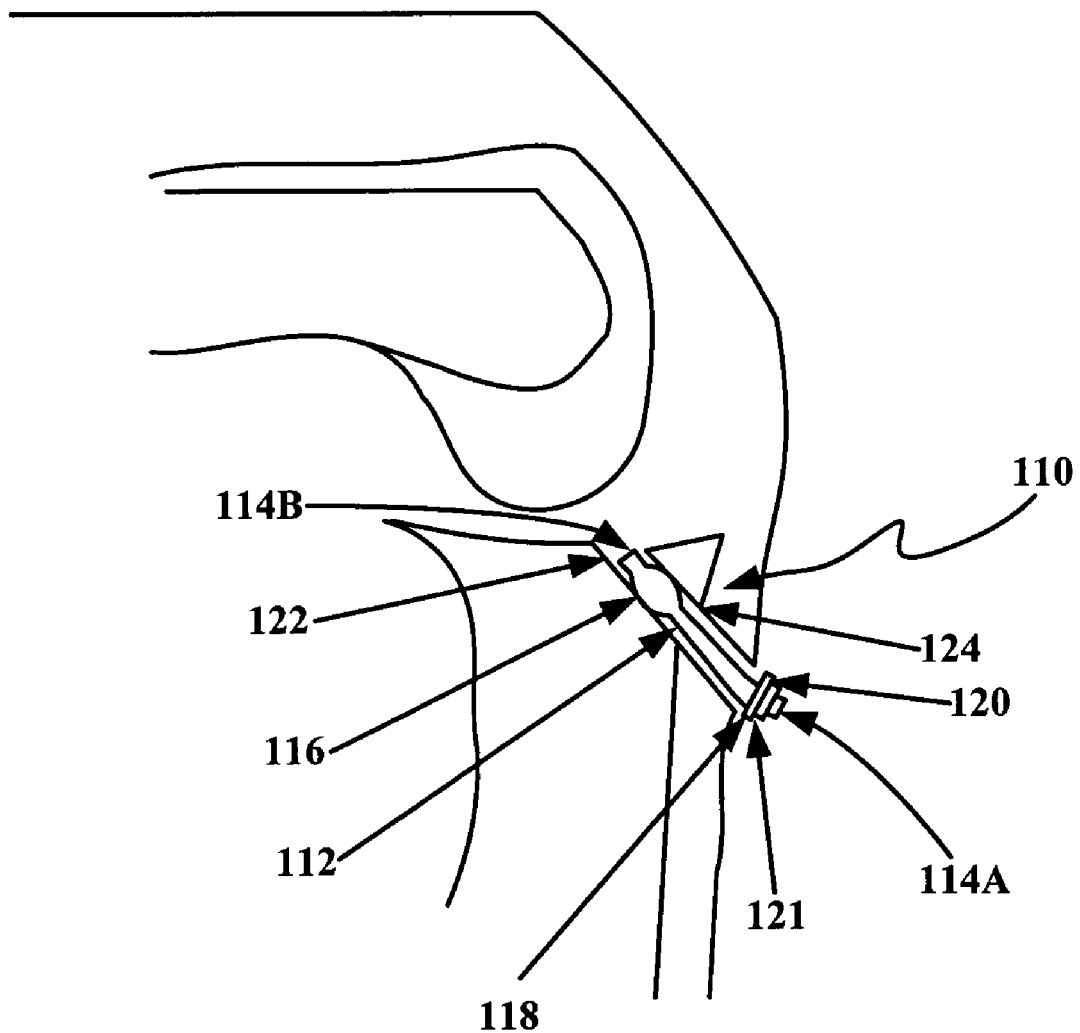
FIG. 6 is a schematic perspective view showing placement of a surgical access device in a tibial tunnel, in accordance with the second exemplary embodiment of the invention.

FIG. 6 is a schematic perspective view showing placement of a surgical access device 110 in a tibial tunnel 122, in accordance with the second exemplary embodiment of the invention. In the second exemplary embodiment, a seal frame 120 may be integral with the access opening 118, outside of the tibial tunnel 122. The seal frame 120 may include a seal 121, which may be comprised of a permeable septum made of rubber material, such as silicone, although other biocompatible elastomeric materials may be used or other self-sealing membranous materials may be used. The access opening 118, at a widest area, may be of greater diameter than an opening to the tibial tunnel 122. By firmly placing the malleable bulbous exterior region 116 against the inner wall of the tibial tunnel 122, the malleable bulbous exterior region 116 may significantly reduce the leaking of fluids from the tibial tunnel 122. The tubular housing 112 may protect a crest 124 of the tibial tunnel 122 from the surgical instruments that are inserted into and removed from the surgical access device 110.

It should be emphasized that the above-described embodiments of the present invention, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

The invention claimed is:

1. A surgical access device, comprising:
   a tubular housing having two ends, each end having an opening there-through;
   a malleable, constantly bulbous exterior region along a portion of the tubular housing; and
   a contiguous seal within the tubular housing, wherein the surgical access device does not have an inflation element.

2. The surgical access device of claim 1, wherein the seal is at a proximal end of the tubular housing and the malleable, constantly bulbous exterior region is located toward a distal end of the tubular housing.

3. The surgical access device of claim 1, wherein the tubular housing further comprises a circular cross-section.

4. The surgical access device of claim 1, wherein the tubular housing and the malleable, constantly bulbous exterior region further comprise a biocompatible, elastomeric material.

5. The surgical access device of claim 1, wherein the tubular housing and the malleable, constantly bulbous exterior region further comprise a medical-grade silicone.

6. The surgical access device of claim 1, wherein the seal comprises a permeable septum.

7. The surgical access device of claim 1, wherein a housing outer diameter of the tubular housing is approximately less than 8 mm and a bulbous outer diameter of the malleable, constantly bulbous exterior region is at least 12 mm.

8. A method of using a surgical access device, the method comprising the steps of:
   at least partially drilling a hole into a bone, the drilling creating a bone tunnel;
   inserting a tubular housing within the bone tunnel, wherein a malleable, constantly bulbous exterior region of the tubular housing is inserted into the bone tunnel in a bulbous-state and sits pressed against an inner wall of the bone tunnel;
   reaching medical instruments through a contiguous seal in the tubular housing thereby engaging in medical activities; and
   removing the tubular housing, wherein the surgical access device does not have an inflation element.

9. The method of claim 8, wherein the step of inserting a tubular housing within the bone tunnel, wherein a malleable bulbous exterior region of the tubular housing sits pressed against an inner wall of the bone tunnel, further comprises adapting a shape of the malleable bulbous exterior region to fit the inner wall of the bone tunnel.

10. The method of claim 8, further comprising the step of dimensioning the tubular housing to fit within the bone tunnel to force against the inner wall of the bone tunnel before inserting the tubular housing within the bone tunnel.

* * * * *